(12) United States Patent
Currier et al.

(10) Patent No.: US 7,857,835 B2
(45) Date of Patent: Dec. 28, 2010

(54) METHOD AND SYSTEM FOR TRANS-LAMINA SPINAL FIXATION

(75) Inventors: Bradford L. Currier, Rochester, MN (US); Carl Lauryssen, Beverly Hills, CA (US); Michael O'Brien, Pinecrest, FL (US); Gerald M. Towns, North Yorkshire (GB)

(73) Assignee: DePuy Spine, Inc., Raynham, MA (US)

( * ) Notice: Subject to any disclaimer, the term of this patent is extended or adjusted under 35 U.S.C. 154(b) by 115 days.

(21) Appl. No.: 12/035,684

(22) Filed: Feb. 22, 2008

(65) Prior Publication Data

US 2009/0216272 A1  Aug. 27, 2009

(51) Int. Cl.
*A61B 17/88* (2006.01)
(52) U.S. Cl. ...................... 606/279; 606/250
(58) Field of Classification Search ......... 606/246–279, 606/300–321
See application file for complete search history.

(56) References Cited

U.S. PATENT DOCUMENTS

2007/0088358 A1*  4/2007  Yuan et al. .................. 606/61
2008/0249570 A1* 10/2008  Carson et al. .............. 606/264
2009/0105760 A1*  4/2009  Frey ........................... 606/246

FOREIGN PATENT DOCUMENTS

| EP | 1774919 A1 | 4/2007 |
|---|---|---|
| WO | 2007044836 A2 | 4/2007 |
| WO | 2008013539 A2 | 1/2008 |

OTHER PUBLICATIONS

European Search Report dated Jun. 10, 2009 for EP09152085.
European Search Report dated Jan. 7, 2010 for EP09152085.
Australian Office Action dated Jan. 29, 2010 for Application No. 2009200671.

* cited by examiner

*Primary Examiner*—Eduardo C Robert
*Assistant Examiner*—Christina Negrelli
(74) *Attorney, Agent, or Firm*—Nutter McClennen & Fish LLP

(57) ABSTRACT

A method of providing spinal stabilization is provided herein. More specifically, the method includes positioning a plurality of fixation assemblies within a plurality of vertebrae in a trans-lamina orientation wherein each fixation assembly includes a proximal portion configured to securely receive a stabilization element (e.g., a stabilization rod). The proximal portions of the various fixation assemblies can be aligned so as to secure at least one stabilization element in a desired position (e.g., along and above a midline of the patient's spine, adjacent and parallel to the midline). A system for providing spinal stabilization is also provided which utilizes trans-lamina delivery and positioning of fixation assemblies within target vertebrae thereby providing stronger fixation and a significant reduction in associated tissue damage.

20 Claims, 7 Drawing Sheets

Prior Art

METHOD AND SYSTEM FOR TRANS-LAMINA SPINAL FIXATION

FIELD OF USE

The present disclosure relates to spinal fixation procedures, in particular to methods and systems of securely positioning spinal fixation assemblies within vertebra(e).

BACKGROUND

Spinal fixation procedures are utilized to align and/or fix desired relationships between adjacent vertebral bodies. Such procedures typically include positioning a plurality of spinal fixation assemblies within target vertebrae. These assemblies usually include a threaded shank portion configured to be disposed (e.g., threaded) within a vertebra and a proximal receiving head configured to receive and secure some type of spinal stabilization element (e.g., a rigid rod, a cable, a biological construct, etc.). Once these assemblies are disposed within the desired vertebrae, the spinal stabilization rod can be positioned and secured within the receiving heads thereby allowing the rod to extend along a length of the patient's spinal column. Once secured as such, the installed spinal stabilization rod can hold the vertebrae in the desired spatial relationship, either until desired healing or spinal fusion has taken place, or for some longer period of time.

Due to the intricacies of working in the proximity of the spinal column, such procedures can result in serious patient injury and/or in significant patient trauma. For example, such procedures typically require the spinal fixation assemblies to be delivered directly (i.e., substantially perpendicular to the midline of the patient's spinal column) into a lateral mass of a target vertebra. In light of this trajectory, significant amounts of muscle and tissue must be stripped from the treatment site due to the relatively large distance between the lateral mass entry point and the midline of the spinal column. Also, any slight miscalculation in the delivery trajectory can result in penetration of a distal portion of the assembly (e.g., a pointed tip) into the spinal canal thereby causing significant patient injury. As a further disadvantage, the limited bone mass and/or bone density typically found in the lateral mass portion of a vertebra significantly limits the amount of area available for contacting the fixation assembly thereby hindering the ability to effectively position the fixation assembly within the vertebra.

Thus, there remains a need for methods and systems capable of securely positioning fixation assemblies within target vertebrae while also minimizing the risk of injury and associated patient trauma.

SUMMARY

Methods and systems for effectively positioning spinal fixation assemblies within target vertebrae while also reducing any associated patient trauma (e.g., muscle stripping, tissue damage, etc.) are provided herein. More specifically, the presently disclosed embodiments utilize trans-lamina delivery and positioning of fixation assemblies within target vertebrae. As described below, trans-lamina delivery provides numerous advantages relative to traditional direct delivery techniques. For example, trans-lamina delivery significantly increases the surface area of vertebral bone available to contact the fixation assembly thereby allowing for the use of larger (e.g., longer and/or wider) fixation assemblies which can enable a stronger, more secure fixation. Additionally, trans-lamina delivery and positioning of the fixation assembly within the vertebra allows each fixation assembly to enter the vertebra at a location significantly closer to a midline of a patient's spinal column as opposed to traditional direct delivery techniques thereby resulting in significantly less tissue and/or muscle damage. Also, the trans-lamina trajectory reduces the risk of injury resulting from penetration of the assembly into the spinal canal because, in contrast to traditional direct delivery techniques the assembly can be angled away from the patient's spinal column during delivery rather than being delivered along a substantially perpendicular trajectory.

Various aspects of a method of providing spinal stabilization are disclosed herein. In one such aspect, the method includes positioning a first fixation assembly within a first vertebra in a trans-lamina orientation and positioning a second fixation assembly within a second vertebra in a trans-lamina orientation such that a proximal receiving head of the first fixation assembly is aligned with a proximal receiving head of the second fixation assembly. Next, the method can include positioning a spinal stabilization element within the proximal receiving heads of both the first and second fixation assemblies and securing the stabilization element (e.g., rod) within each of the proximal receiving heads.

The fixation assemblies can be positioned within any number and/or type (e.g., cervical, thoracic, lumbar) of vertebra as required by any given procedure. Also, the method can include positioning the fixation assemblies in various manners so as to optimize the orientation of the stabilization element (e.g., stabilization rod) relative to the patient's spinal column. For example, in one such embodiment, the proximal receiving heads of the various fixation assemblies can be positioned along and over the midline of a patient's spinal column such that a single stabilization element can be coupled thereto which allows the stabilization element to be positioned along and over the midline of the patient's spinal column. In other embodiments, the proximal receiving heads of each of a first plurality of fixation assemblies can be positioned along one side of the midline of a patient's spinal column, and the proximal receiving heads of each of a second plurality of fixation assemblies can be positioned on the opposite side of the midline of the patient's spinal column. In such an embodiment, a first stabilization element can be coupled to the receiving heads of each of the first plurality of fixation assemblies, and a second stabilization element can be coupled to the proximal receiving heads of each of the second plurality of fixation assemblies thereby positioning the stabilization elements on opposite sides of the midline of the patient's spinal column. Thus, such trans-lamina delivery and positioning of the fixation assemblies allow for increased stability as well as versatility in positioning of the stabilization element(s) relative to the patient's spinal column.

The method can also include various procedures for further optimizing the delivery and positioning of the fixation assemblies within the vertebrae. For example, the method can include removing various portions of at least one (or all) target vertebra prior to engagement of the fixation assembly. Such truncation can be utilized to better position the proximal end(s) of the fixation assembl(ies) relative to a stabilization element and/or to facilitate engagement of the fixation assembl(ies) to the vertebra(e) by providing access to an optimal portion of the vertebral bone. For example, the method can include removal or truncation of the spinous process of the vertebra(e) thereby allowing for positioning of the proximal end(s) of the assembl(ies) along the midline of the patient's spinal column.

The spinal fixation assembl(ies) can be configured in various manners. In general, the assemblies can include any type of assembly configured to securely engage a vertebra, and also having a proximal portion configured to securely receive a stabilization element. For example, the fixation assembly can include a bone anchor element (e.g., a bone screw) having a proximal end which is coupled to a receiving head configured to receive and secure a stabilization element thereto. In an exemplary embodiment, the receiving head is movably coupled to the bone anchor element. For example, the receiving head can be capable of polyaxial motion relative to the bone anchor. Additionally, the receiving head can be configured in virtually any manner capable of receiving and securing the stabilization element. In an exemplary embodiment, the receiving head can include a "U-shaped" opening configured to receive the stabilization element. In such an embodiment, the U-shaped opening of the receiving head can include various internal threads (or other engagement means) configured to receive any type of closure mechanism (e.g., a set screw) having a corresponding set of threads thereby securing the stabilization element to the assembly.

In another aspect, a method of providing spinal stabilization is provided which includes positioning a plurality of fixation assemblies within a plurality of vertebrae wherein the fixation assemblies are positioned within the vertebrae in a trans-lamina orientation. In an exemplary embodiment, each fixation assembly can include a threaded shank with a proximal end polyaxially coupled to a receiving head. Next, the method can include securing a first stabilization element within the receiving head of a first fixation assembly and also within a receiving head of a second fixation assembly thereby positioning the stabilization element adjacent a midline of a patient's spinal column. Optionally, the method can also include securing a second stabilization element within a receiving head of a third fixation assembly and also within a receiving head of a fourth fixation assembly thereby positioning the second stabilization element adjacent a midline of a patient's spinal column and on an opposite side of the midline as compared to the first stabilization element.

Various aspects of a system of providing spinal stabilization are also disclosed herein. In one such aspect, the system includes a plurality of fixation assemblies secured to a plurality of vertebrae in a trans-lamina orientation wherein each fixation assembly includes a bone anchor element movably coupled to a receiving head. The system further includes a stabilization element (e.g., a rod, cable, etc.) capable of being secured within a plurality of such receiving heads such that the stabilization element can be positioned in a substantially parallel orientation relative to a midline of a patient's spine. Like above, the stabilization element(s) can be positioned at various locations relative to the patient's spinal column. For example, the system can include a stabilization element positioned along and above the midline of the patient's spine. In other embodiments, the system can include a stabilization element(s) positioned adjacent the midline of the patient's spine. For example, the system can include first and second spinal stabilization elements positioned on opposite sides of the midline of a patient's spinal column.

These and other aspects of the presently disclosed methods and systems are detailed below.

BRIEF DESCRIPTION OF THE DRAWINGS

The presently disclosed embodiments will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the system and method disclosed herein. One or more examples of these embodiments are illustrated in the accompanying drawings. Those skilled in the art will understand that the system and method described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Methods and systems for spinal stabilization utilizing trans-lamina delivery and positioning of fixation assemblies within target vertebrae are provided herein. In contrast to traditional direct delivery of fixation assemblies into the lateral mass, trans-lamina delivery increases the amount of vertebral bone available to receive the fixation assembly thereby providing for a stronger fixation and improved therapeutic results. Also, the larger amount of vertebral bone available enables the use of larger (e.g., longer and/or wider) fixation assemblies which also facilitates a stronger fixation. Trans-lamina delivery and positioning of the fixation assemblies also significantly reduces the amount of tissue and/or muscle damage resulting from the procedure because the fixation assembly can enter the target vertebra at a location closer to the midline of a patient's spinal column as compared to traditional direct delivery procedures. As a further advantage, the delivery trajectory made available by such trans-lamina delivery and positioning reduces the potential for inadvertent damage to the spine and/or surrounding areas because the assemblies can be angled away from the patient's spinal canal during delivery.

Figure 1A:
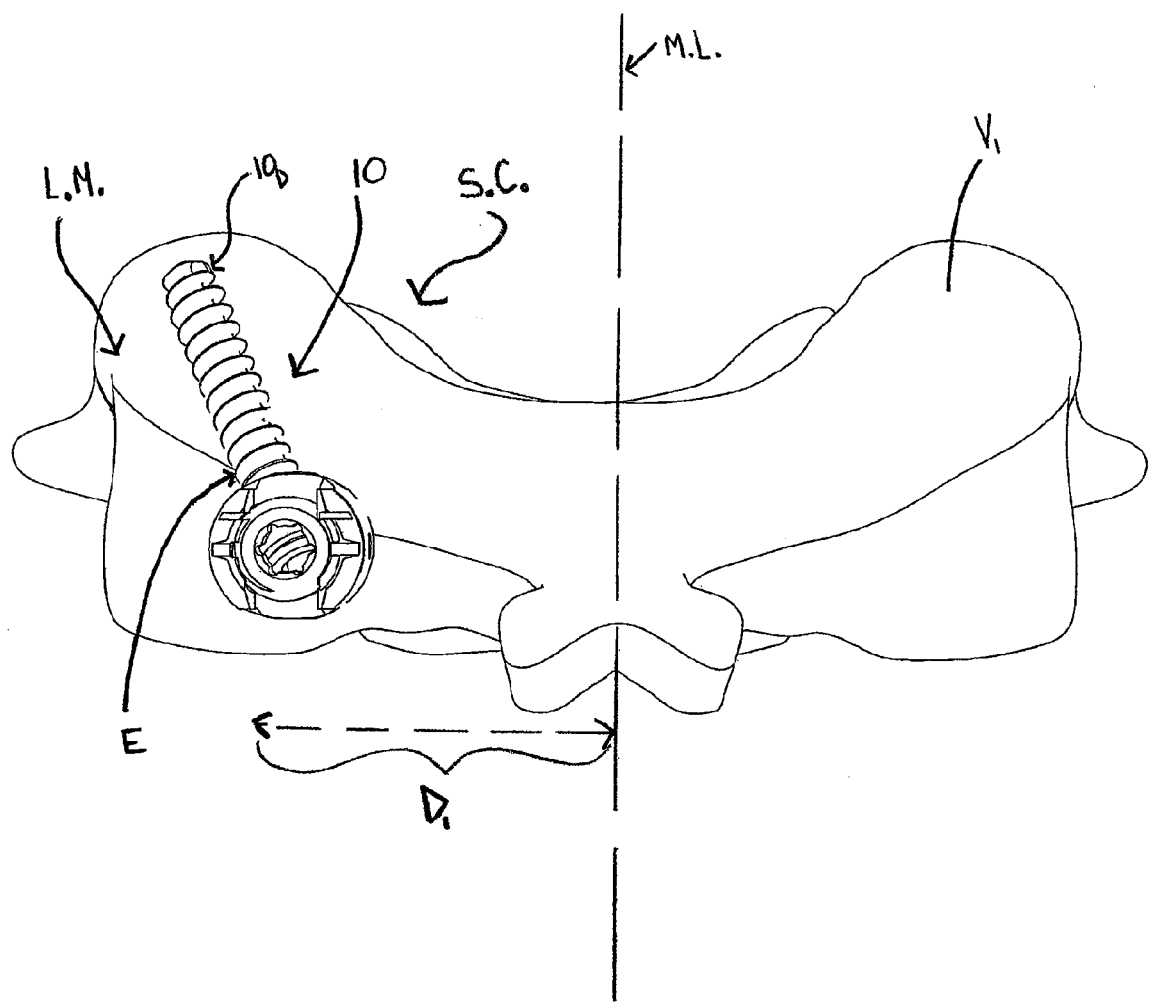
FIG. 1A is a perspective view of a prior art procedure wherein a fixation assembly is delivered directly into a lateral mass of a target vertebra.
Figure 1B:
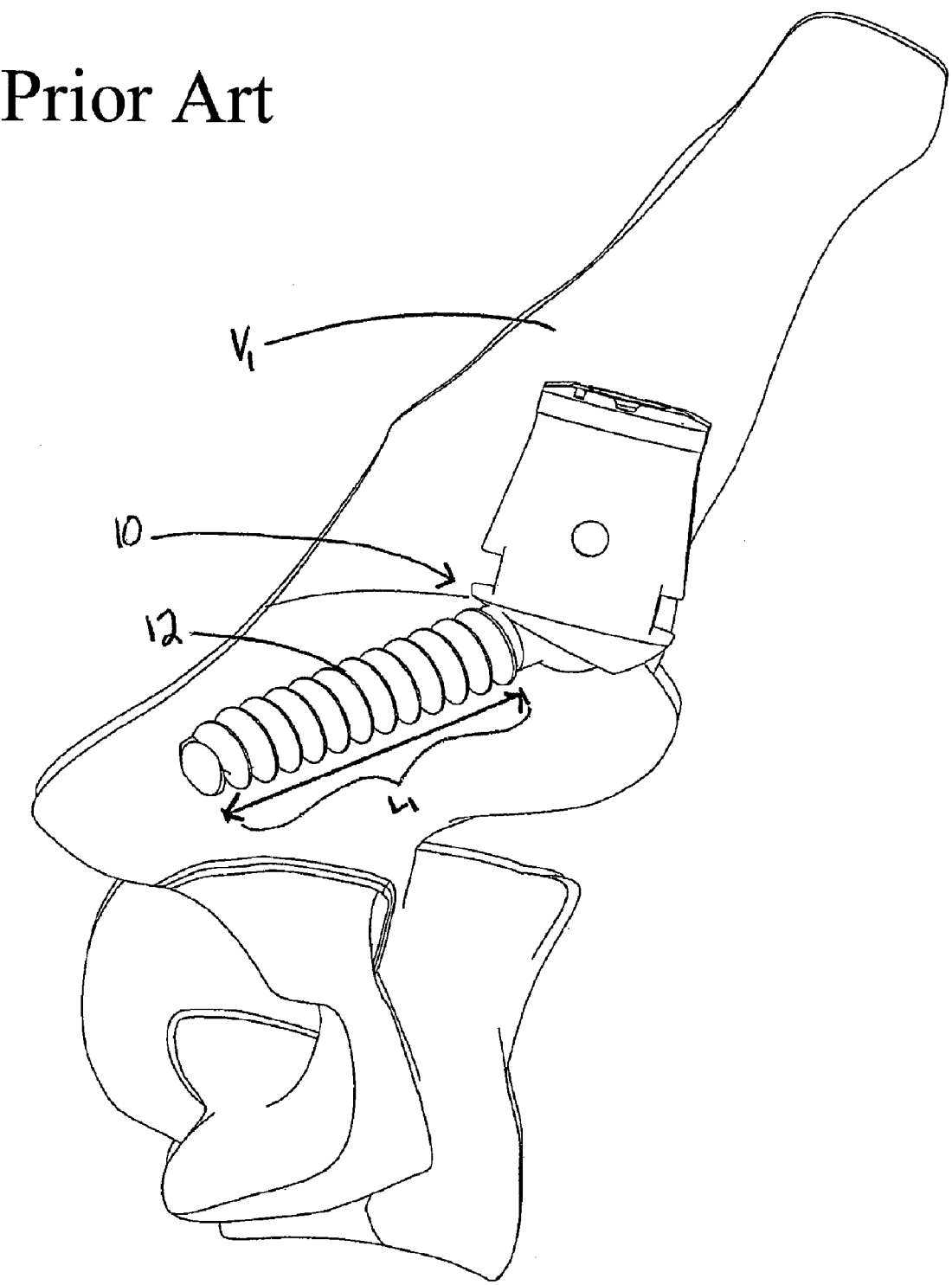
FIG. 1B is another view of the direct delivery technique illustrated in FIG. 1A.

FIGS. 1A and 1B illustrate a traditional spinal fixation technique wherein a fixation assembly 10 is directly delivered to and positioned within the lateral mass (L.M.) of a target vertebra $V_1$. As shown, direct delivery of the fixation assembly 10 to the lateral mass (L.M.) significantly limits the usable entry points (E) for the fixation assembly 10 because the user must ensure against penetration of the fixation assembly 10 into the spinal canal (S.C.) and/or surrounding nerves. As shown, any slight miscalculation in delivery trajectory can result in unwanted introduction of the distal end $10_D$ of the assembly 10 into the spinal canal (S.C.). Additionally, the traditional approach typically results in significant tissue damage because the fixation assembly 10 must be delivered to the vertebra $V_1$ at an entry point (E) which is a relatively large distance ($D_1$) away from the midline (M.L.) of the patient's spinal column. Thus, to provide access to the entry point (E), the procedure requires significant amounts of muscle and/or tissue stripping. As a further drawback, in light of the relatively small amount of vertebral bone present in the lateral mass (L.M.), the procedure is typically limited to fixation assemblies having a relatively short length ($L_1$) thereby hindering the ability to provide a strong fixation between assembly 10 and the target vertebra $V_1$.

Figure 2:
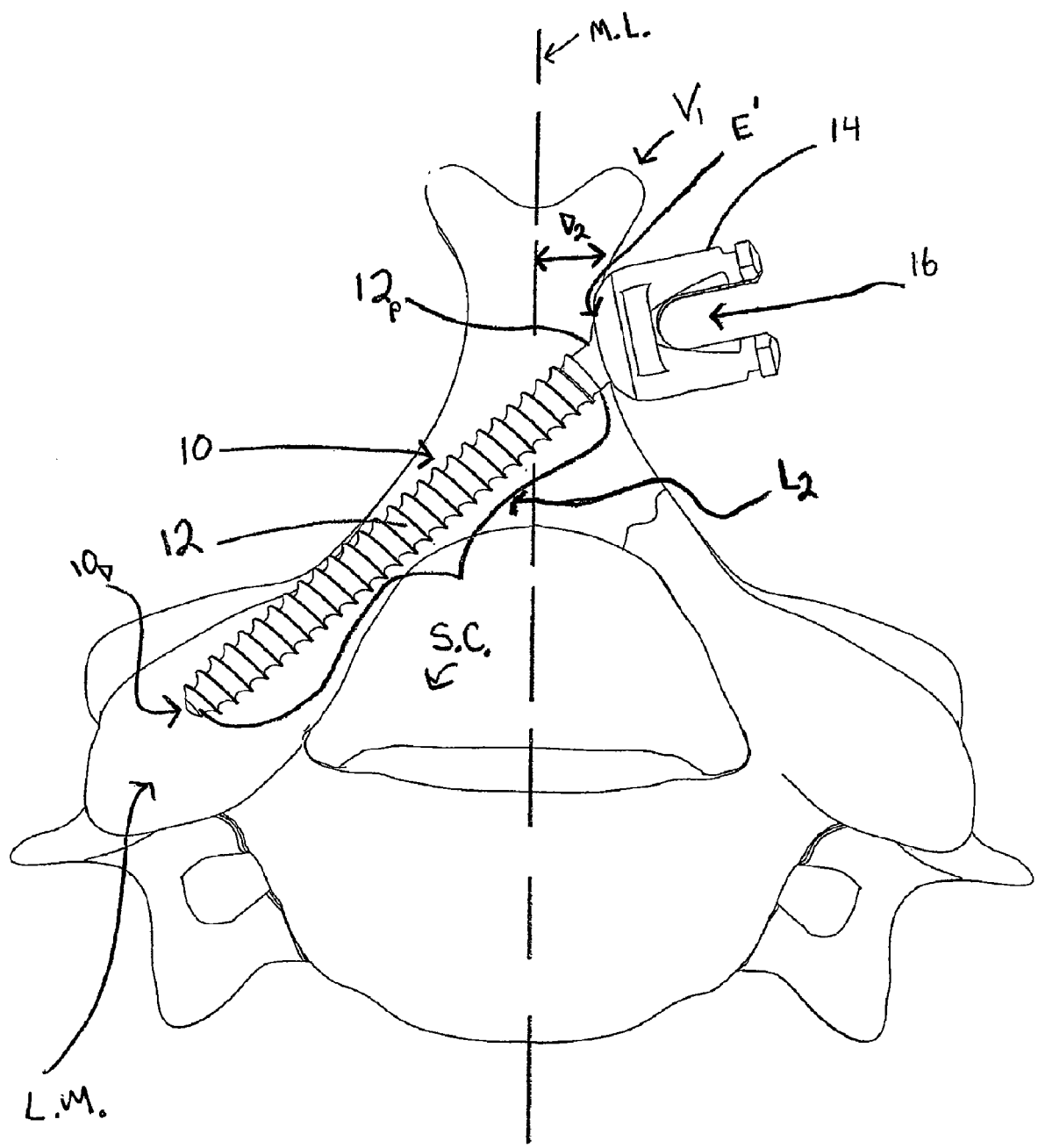
FIG. 2 is a representation showing a fixation assembly positioned within a target vertebra in a trans-lamina orientation.
Figure 3A:
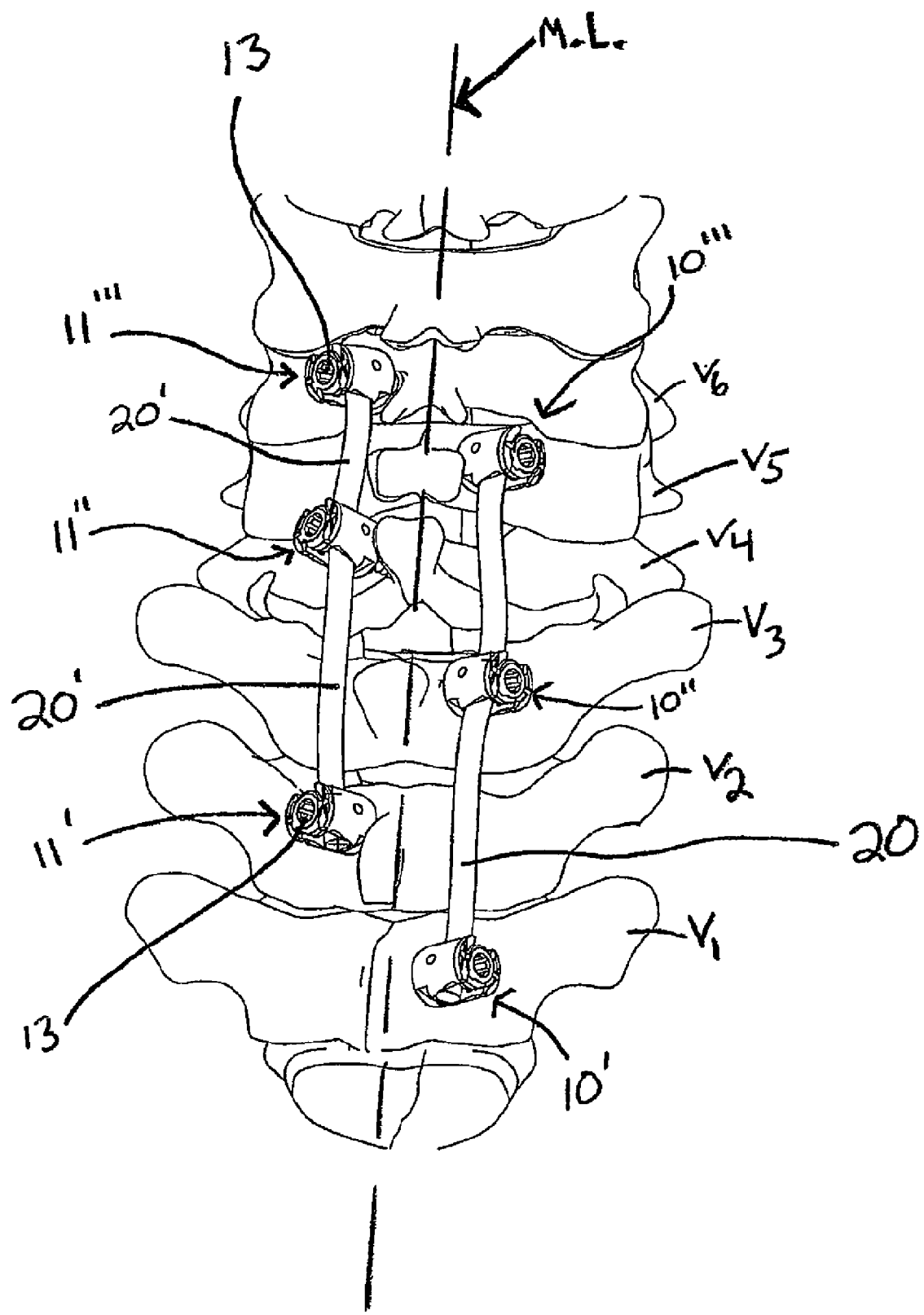
FIG. 3A is a view of an embodiment wherein a plurality of fixation assemblies are positioned within vertebrae in a trans-lamina orientation.
Figure 4A:
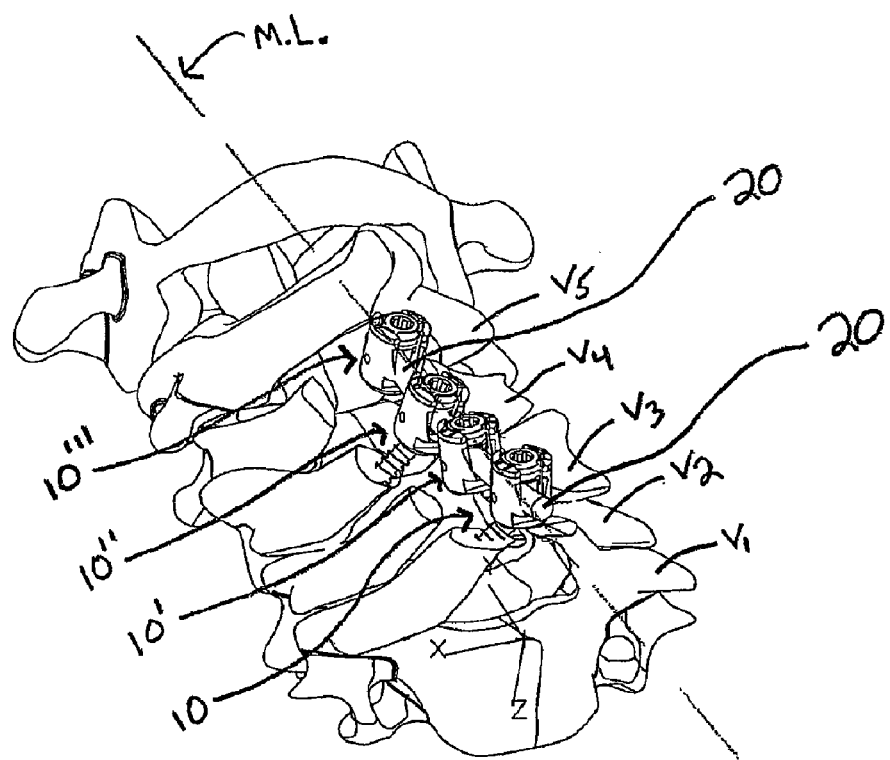
FIG. 4A is a perspective view of an embodiment wherein a spinal stabilization element is positioned along and above a midline of a patient's spinal column.
Figure 4B:
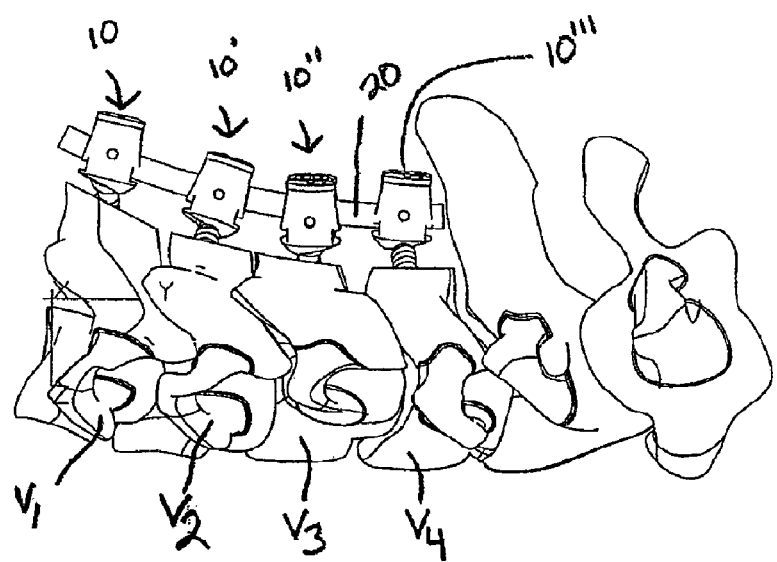
FIG. 4B is a side view of the embodiment of FIG. 4A.
Figure 5:
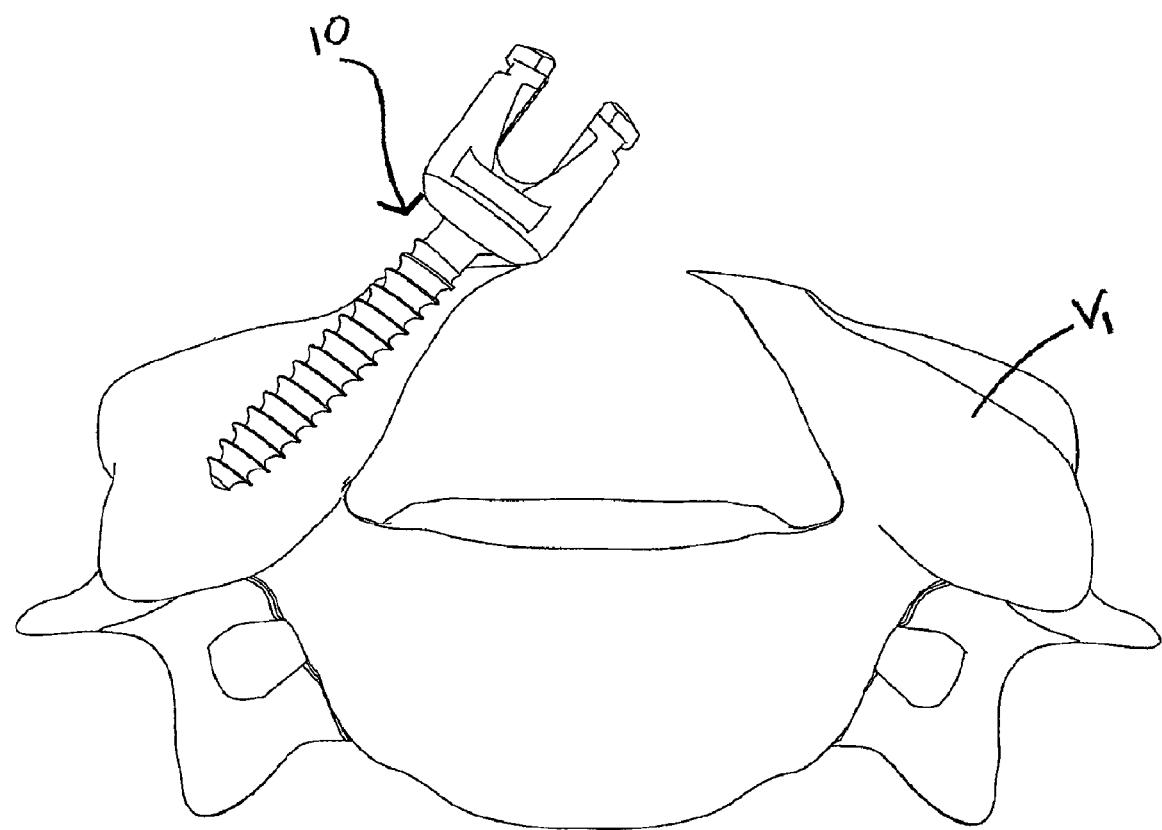
FIG. 5 is a view of an embodiment wherein portions of a vertebra have been truncated prior to trans-lamina delivery and positioning of the fixation assembly.

In contrast, FIG. 2 shows an exemplary embodiment of the presently disclosed method wherein a spinal fixation assembly 10 is delivered and positioned within a target vertebra $V_1$ in a trans-lamina orientation. That is, the fixation assembly 10 is delivered across a lamina portion of the vertebra $V_1$ and into the lateral mass (L.M.). As will be described, such a trajectory can allow at least a portion of the fixation assembly 10 to be positioned above the midline (M.L.) of the patient's spinal column (S.C.). For example, in those procedures which require positioning a stabilization rod offset from the midline (M.L.) of the spinal column (as shown in FIGS. 2 and 3A), the fixation assembly can be delivered and positioned within the vertebra $V_1$ in a trans-lamina orientation such that a threaded shank 12 of the fixation assembly 10 crosses over the midline (M.L.) of the spinal column (S.C.). Similarly, in those procedures requiring the placement of a stabilization rod along and above the midline (as shown in FIGS. 4A-4B), trans-lamina delivery can allow for a proximal receiving head of the fixation assembly 10 to be positioned substantially over the midline (as shown in FIG. 5).

The presently disclosed trans-lamina fixation procedures provide numerous benefits over the above-described direct delivery approach. For instance, such trans-lamina delivery and positioning allows for a stronger fixation between the fixation assembly 10 and corresponding vertebral bone $V_1$ because a larger surface area and/or denser bone mass can be utilized to receive and engage the fixation assembly 10. In light of the enlarged surface area, the fixation assembly 10 can include a larger (e.g., longer and/or wider) bone anchor element 12 which also contributes to a stronger fixation. Additionally, trans-lamina delivery and positioning significantly reduces the risk of injury because the distal end of the fixation assembly $10_D$ can be angled away from the spinal canal (S.C.) during delivery as opposed to the prior art trajectory which is substantially perpendicular to the spinal column (S.C.). Additionally, in utilizing trans-lamina delivery and positioning, the assembly 10 can enter the vertebrae $V_1$ at a trans-lamina entry point (E') which is a substantially shorter distance ($D_2$) from the midline (M.L.) of the spinal column as compared to the distance ($D_1$, shown in FIG. 1A) required when utilizing the traditional direct delivery approach. Thus, the presently disclosed trans-lamina delivery and positioning of fixation assemblies 10 within vertebrae $V_1$ significantly reduces any associated tissue and/or muscle damage as compared to the traditional approach.

As will be appreciated by those skilled in the art, the fixation assembly 10 can be virtually any type of assembly having a distal portion 12 configured to engage vertebral bone $V_1$ and having a proximal portion 14 configured to securely receive some type of spinal stabilization element (e.g., a stabilization rod). For example, referring again to FIG. 2, the fixation assembly 10 can include a bone anchor element 12 configured to securely engage vertebral bone $V_1$. As will be appreciated by those skilled in the art, the bone anchor element 12 can be any type of element configured to engage vertebral bone. In an exemplary embodiment, the bone anchor element 12 is a bone screw 12 having a thread extending along a portion of the screw 12 thereby allowing the element 12 to be effectively delivered to and securely positioned within the vertebra $V_1$. While the bone anchor element 12 can include a wide range of sizes and/or shapes, as indicated above, an advantage of trans-lamina delivery is the ability to utilize larger elements 12 as compared to the traditional approach. For example, FIG. 2 shows an embodiment of a bone anchor element 12 having a length ($L_2$) substantially longer than the length ($L_1$) of the bone screw utilized in the traditional technique depicted in FIG. 1B.

Again referring to FIG. 2, the proximal portion 14 of the fixation assembly 10 can be configured in various manners to securely engage a spinal stabilization element (e.g., a stabilization rod). For example, the fixation assembly 10 can include a receiving head 14 coupled to a proximal end of the bone anchor element 12p. Such a receiving head 14 can be configured to securely receive the spinal stabilization element in various manners. For example, in an exemplary embodiment, the receiving head 14 can include a "U"-shaped opening 16 configured to receive the stabilization element. In other embodiments, the opening 16 can include various other shapes capable of receiving the stabilization element. The receiving head 14 can also be configured in various manners so as to secure the stabilization element therein. For example, the receiving head 14 can include various internal threads (not shown) capable of receiving a closure mechanism 13 (see FIG. 3A) thereby securing the stabilization element within the head 14. Those skilled in the art will appreciate that the receiving head 14 can be configured in various manners so as to retain the stabilization element therein.

The fixation assembly 10 can also be configured to allow for movement of the receiving head 14 relative to the bone anchor element 12. While the receiving head 14 can be coupled to the bone anchor element 12 in any number of manners to provide any desired movement and/or range of motion, in an exemplary embodiment, the head 14 is capable of polyaxial movement relative to the element 12. Those skilled in the art will appreciate that the receiving head 14 and/or the proximal end 12p of the bone anchor element 12 can be configured and/or coupled in various such manners so as to provide such polyaxial motion. In other embodiments, the fixation assembly 10 can be configured so as to allow the receiving head 14 to be rotated relative to the bone-engaging element 12 thereby allowing for the openings 16 of the various receiving heads 14 to be aligned relative to one another prior to delivery of the stabilization element.

As shown in FIGS. 3A-4B, following trans-lamina positioning of the various fixation assemblies 10, one or more stabilization elements (e.g., stabilization rods) can be secured thereto to provide the desired therapeutic effect. As will be apparent to those skilled in the art, the stabilization element 20 can be a rod, a cable, a biological construct, etc. Further, the stabilization element 20 can have a wide range of dimensions (e.g., length and/or diameter) and/or shapes (e.g., straight, contoured, etc.) which are selected in accordance with the patient's anatomy and/or the requirements of the surgical procedure. As also shown, the method can include positioning first and second stabilization elements on opposite sides of the midline (M.L.) of the patient's spinal column (as shown in FIGS. 3A-3B) or the method can include positioning a single stabilization element along and above the midline (M.L.) of a patient's spinal column (as shown in FIGS. 4A-4B). These procedures are now discussed in greater detail.

Figure 3B:
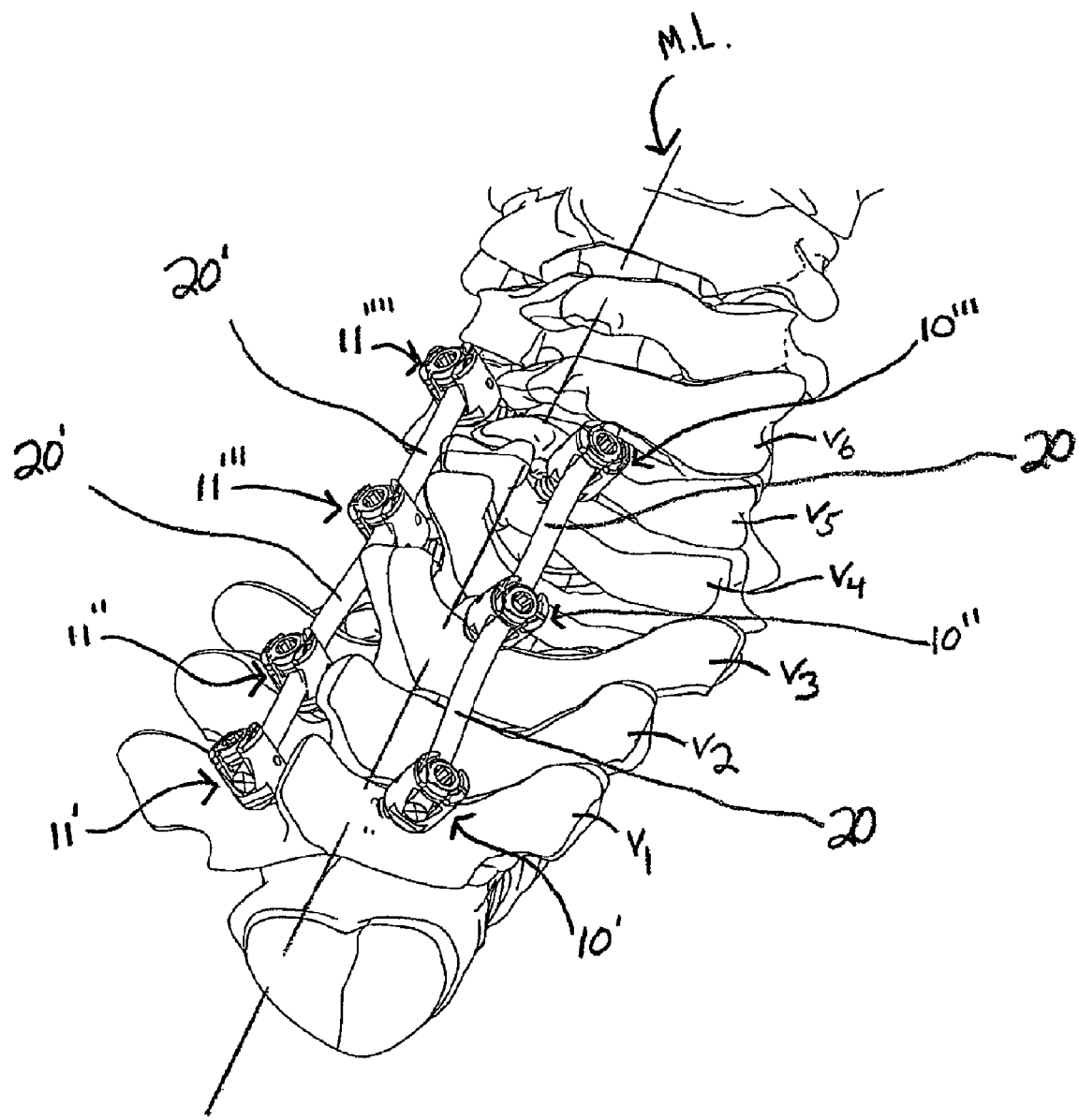
FIG. 3B is a view of another embodiment wherein a plurality of fixation assemblies are positioned within vertebrae in a trans-lamina orientation.

FIGS. 3A and 3B show an exemplary embodiment which includes a plurality of fixation assemblies 10', 10", 10''', 11', 11", 11''' being delivered and positioned within target vertebrae in a trans-lamina orientation. Those skilled in the art will appreciate that these assemblies 10', 10", 10''', 11', 1", 1''' can be delivered to any pattern of vertebrae $V_1, V_2, V_n$ (e.g., every vertebrae, every other vertebrae, every fourth vertebrae, etc). For example, referring to FIG. 3A, the method can include engaging a first plurality of fixation assemblies 10', 10", 10''' to a plurality of vertebrae $V_1, V_3, V_5$ in a trans-lamina orientation such that the proximal portions of these assemblies 10', 10", 10''' are disposed adjacent a midline (M.L.) of the patient's spinal column. The method can further include delivering a second plurality of fixation assemblies 11', 11", 11''' to a plurality of vertebrae $V_2, V_4, V_6$ in a trans-lamina orientation such that the proximal portions of these fixation assemblies 11', 11", 11''' are disposed adjacent the midline (M.L.) of the patient's spinal column and also on the opposite side of the midline (M.L.) as compared to first plurality of fixation assemblies 10', 10", 10'''. Once positioned as such, a first stabilization element 20 can be positioned and secured within the proximal ends of the first plurality of fixation assemblies 10, 10", 10''', and a second stabilization element 20' can be positioned and secured within the proximal ends of the second plurality of fixation assemblies 11', 11", 11'''. Thus, as shown in FIG. 3A, the embodiment provides first and second stabilization elements 20, 20' positioned on opposite sides of the midline (M.L.) of the patient's spine wherein the stabilization elements 20, 20' are substantially parallel to the midline (M.L.) of the spine. In other embodiments, the method can include positioning only one plurality of fixation assemblies 10', 10", 10''' along a single side of the midline (M.L.) of the patient's spine.

As indicated above, the presently disclosed method allows for delivery and positioning of any number of fixation assemblies 10 to any number and/or pattern of vertebrae $V_1$. For example, as shown in FIG. 3A, the first plurality of fixation assemblies 10', 10", 10''' can be positioned in a trans-lamina orientation within every other vertebrae $V_1, V_3, V_5$. Additionally, the second plurality of fixation assemblies 11', 11", 11''' can also be positioned within every other vertebrae $V_2, V_4, V_6$ and staggered with respect to the first plurality of fixation assemblies such that each of the six fixation assemblies 10', 10", 10''', 11', 11", 11''' are positioned within a distinct vertebra $V_1$-$V_6$. In other embodiments, the method can include any number of fixation assemblies (e.g., 2, 3, 4, 5, 6, etc.) configured to receive and secure a stabilization element 20 of any desired length. Additionally, as shown in FIG. 3B, the method can include delivering at least one fixation assembly of the first plurality of fixation assemblies 10' and at least one fixation assembly of the second plurality of fixation assemblies 11' to the same vertebra $V_1$ along trans-lamina trajectories. Additionally, the fixation assemblies of the first and/or second plurality of fixation assemblies 10', 10", 10''', 11', 11", 11''' can be secured to sequential vertebra, every other vertebra, every fourth vertebra, or any other pattern required and/or preferred for a given procedure. Such versatility allows the surgeon to select optimal vertebral locations for delivery and positioning of the fixation assemblies and stabilization elements.

In other exemplary embodiments, the method can include the use of a single stabilization element 20 positioned along and above the midline (M.L.) of a patient's spine. FIGS. 4A and 4B provide an example of such an embodiment wherein a plurality (e.g., four) of fixation assemblies 10, 10', 10", 10''' are delivered in a trans-lamina orientation relative to successive vertebra $V_1, V_2, V_3, V_4$ such that the proximal portions of each assembly 10, 10', 10", 10''' are substantially aligned along and above the midline (M.L.) of the patient's spine. Like above, the fixation assemblies 10, 10', 10", 10''' can be delivered to the vertebrae in various patterns and/or configurations so as to position the proximal portions of the assemblies in the desired location. For example, as shown in FIGS. 4A and 4B, the fixation assemblies 10, 10', 10", 10''' can be delivered such that each bone anchor is angled in a direction opposite of its adjacent bone anchor along successive vertebrae $V_1, V_2, V_3, V_4$. In other embodiments, similar to what is described above, the fixation assemblies 10, 10', 10", 10''' can be delivered to every other vertebra, every fourth vertebra, etc. Also, any number of fixation assemblies 10, 10', 10", etc. can be utilized depending on the patient's anatomy and/or requirements of the procedure. For example, the method can utilize 2, 3, 4, 5, or more fixation assemblies 10. In short, the method can include any number of fixation assemblies positioned within any number and/or pattern of target vertebrae in a trans-lamina orientation so as to securely position at least one stabilization element in a desired location.

Various embodiments of the method can also include modifying and/or truncating various portions of the target vertebrae $V_1$ so as to further optimize the procedure. More specifically, removing various portions of the target vertebra (e) $V_1$ can provide access to an optimal entry point of the vertebral bone and can facilitate positioning of the proximal end of the fixation assemblies 10 at desired locations. For example, FIGS. 4A, 4B and 5 provide an exemplary embodiment wherein portions of various vertebrae ($V_1$-$V_4$ in FIGS. 4A-4B and $V_1$ in FIG. 5) have been removed or truncated thereby allowing the proximal portion of each fixation assembly 10 to be positioned above and along the midline (M.L.) of the patient's spine. Additionally, removing these portions of the target vertebrae $V_1$ can provide an easier target for delivery of the fixation assemblies 10 because the truncated vertebrae $V_1$ can be substantially planar and therefore easier to engage the assemblies 10 thereto. As will be apparent to those skilled in the art, the method can include removing any portion of the vertebra(e) $V_1$ as required by a given procedure. As shown in the exemplary embodiments of FIGS. 4A, 4B, and 5, the method can also include removing (or truncating) the spinous process of all (or at least one) vertebrae $V_1$.

Various embodiments of a system of providing spinal stabilization are also disclosed herein. In an exemplary embodiment, the system can include a plurality of fixation assemblies 10, 10', 10", etc. engaged to a plurality of vertebrae $V_1, V_2, V_3$, etc. in a trans-lamina orientation wherein each fixation assembly 10 includes a bone anchor element (e.g., a bone screw) 12 coupled to a movable receiving head 14. The system can further include a stabilization element (e.g., a rod, cable, etc.) 20 secured within a plurality of such movable heads 14 such that the stabilization element 20 maintains a substantially parallel orientation relative to a midline (M.L.) of a patient's spine. Like above, the stabilization element(s) 10 can be positioned at various locations relative to the patient's spinal column (S.C.). For example, the system can include a stabilization element 20 positioned along and above the midline (M.L.) of the patient's spine. In other embodiments, the system can include a stabilization element(s) 20 positioned adjacent the midline (M.L.) of the patient's spine. For example, the system can include first and second spinal stabilization elements 20, 20' positioned on opposite sides of the midline (M.L.) of a patient's spinal column.

One skilled in the art will appreciate further features and advantages of the presently disclosed method and system based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A method of providing spinal stabilization, comprising:
   positioning a first fixation assembly having a proximal receiving head and a distal shank within a first vertebra in a trans-lamina orientation such that one of the proximal receiving head and the distal shank of the first fixation assembly is on a midline of a patient's spinal column;
   positioning a second fixation assembly within a second vertebra in a trans-lamina orientation such that the proximal receiving head of the first fixation assembly is aligned with a proximal receiving head of the second fixation assembly;
   positioning a spinal stabilization element within the proximal receiving heads of both the first and second fixation assemblies; and
   securing the spinal stabilization element within each of the proximal receiving heads.

2. The method of claim 1, wherein the proximal receiving head of each fixation assembly is positioned along and above the midline of the patient's spinal column.

3. The method of claim 1, wherein the proximal receiving head of each fixation assembly is positioned adjacent the midline of the patient's spinal column.

4. The method of claim 1, further comprising:
   removing a portion of at least one vertebra; and
   positioning the fixation assembly within the at least one vertebra in a trans-lamina orientation.

5. The method of claim 4, wherein the spinous process of the vertebra is removed.

6. The method of claim 5, wherein the proximal receiving head of each fixation assembly is positioned along and above the midline of the patient's spinal column.

7. The method of claim 1, wherein the fixation assemblies are positioned within adjacent vertebrae.

8. The method of claim 1, wherein the fixation assemblies are positioned within non-adjacent vertebrae.

9. The method of claim 1, wherein each receiving head is configured for polyaxial motion.

10. The method of claim 1, wherein each receiving head includes a U-shaped opening configured to securely receive a stabilization element.

11. A method for providing spinal stabilization, comprising:
    positioning a plurality of fixation assemblies within a plurality of vertebrae, each fixation assembly having a threaded shank with a proximal end polyaxially coupled to a receiving head, the fixation assemblies being positioned within the vertebrae in a trans-lamina orientation such that one of the threaded shank and the receiving head of each fixation assembly is on a midline of a patient's spinal column; and
    securing a first stabilization element within the receiving head of a first fixation assembly and the receiving head of a second fixation assembly thereby positioning the stabilization element adjacent the midline of the patient's spinal column.

12. The method of claim 11, further comprising:
    securing a second stabilization element within the receiving head of a third fixation assembly and the receiving head of a fourth fixation assembly thereby positioning the second stabilization element adjacent the midline of the patient's spinal column and on an opposite side of the midline as compared to the first stabilization element.

13. The method of claim 11, wherein the first and second stabilization elements are stabilization rods.

14. The method of claim 11, wherein at least one of the plurality of vertebrae is a cervical vertebra.

15. The method of claim 11, wherein the stabilization element extends along at least three vertebrae.

16. A system for providing spinal stabilization, comprising:
    a plurality of fixation assemblies, each fixation assembly configured to be implanted within a vertebra in a trans-lamina orientation, each fixation assembly having a bone-engaging element coupled to a movable receiving head, wherein the bone-engaging element is configured to be delivered across a lamina and into a lateral mass of the vertebra such that a distal end of the bone-engaging element is positioned contralateral to the receiving head; and
    a stabilization element secured within each movable receiving head such that the stabilization element maintains a substantially parallel orientation relative to a midline of a patient's spine.

17. The system of claim 16, wherein the stabilization element is configured to be positioned along and above the midline of the patient's spine.

18. The system of claim 16, wherein the stabilization element is configured to be positioned adjacent the midline of the patient's spine.

19. The system of claim 18, further comprising:
    a second stabilization element secured within a second plurality of movable receiving heads such that the second fixation assembly is configured to be positioned adjacent the midline of the patient's spine and on the opposite side of the midline relative to the first spinal stabilization element.

20. The system of claim 16, wherein the stabilization element is a rod.

* * * * *